United States Patent [19]

Harrington et al.

[11] 4,268,504

[45] May 19, 1981

[54] COMPOSITION AND METHOD FOR THE TREATMENT OF ANIMAL HOOVES

[76] Inventors: John G. Harrington, 58913 Carmelita Cir., Yucca Valley, Calif. 92284; William W. Hornbeck, P.O. Box 461, Mira Loma, Calif. 91752

[21] Appl. No.: 80,080

[22] Filed: Sep. 28, 1979

Related U.S. Application Data

[63] Continuation-in-part of Ser. No. 841,301, Oct. 12, 1977, abandoned.

[51] Int. Cl.³ ..................... A61K 33/34; A61K 33/00
[52] U.S. Cl. ........................................ 424/143; 119/1; 424/127; 424/145; 424/147; 424/144; 424/154
[58] Field of Search ................... 119/1; 424/127, 143, 424/145, 147, 144, 154

[56] References Cited

U.S. PATENT DOCUMENTS 2,179,591  11/1939  Godchaux .............................. 119/1
4,008,688   2/1977  Nicholas ................................ 119/1

OTHER PUBLICATIONS

Miller et al.–Encyclopedia of Animal Care, (1962), pp. 341, 345, 346 and 419.
Winslow–Veterinary Materi Medica & Therapeutics––Eighth edit. (1919) pp. 131–133, 145–148 and 154–155.

*Primary Examiner*—Sam Rosen
*Attorney, Agent, or Firm*—Boniard I. Brown

[57] ABSTRACT

A novel composition, useful for the treatment of animal hooves for the purpose of killing bacteria, healing infections, thickening and hardening sole and frog as well as a novel method for treating animal hooves, is disclosed.

12 Claims, No Drawings

4,268,504

COMPOSITION AND METHOD FOR THE TREATMENT OF ANIMAL HOOVES

RELATED APPLICATIONS

This application is a continuation-in-part of application Ser. No. 841,301, filed Oct. 12, 1977, now abandoned.

FIELD OF THE INVENTION

This invention is related to the field of animal patent medicines or preparations in general and more particularly to chemical preparations useful for the treatment of various animal hoof infections and maladies.

BACKGROUND AND PRIOR ART

Domestic animals and others belonging to the Equidae-, and Bovidae- families are susceptible to maladies and infections of the hooves, occasioned by the presence of bacteria in the soil, cuts and/or bruises, which require special treatment to cure or eliminate. Presently these disorders are chemically treated by applying various ingredients in the form of salves, ointments and sprays directly to the affected area on the particular animal, or by the injection of antibiotics directly into the blood stream of the animal.

Typical chemicals used for the treatment of animal hoofs include, but are not limited to; Sulfathiazol and urea; a paste sold under the tradename "Sulfurea"; Sulfubromethazine, a paste sold under the tradename "Sulfubrom"; Nitrofurazone, a liquid or paste sold under the tradename "Furacin"; Lead Acetate, a liqiuid sold under the tradename "Burrow's Solution"; a mixture of various oils, compounded into a spray and sold under the tradename "Hoof Coat" and Copper Naphthenate sold as "Thrush X" for the treatment of thrush of the feet.

Each of the above-mentioned prior art compounds are similar in that a direct application of the compounds, in the form of a spray, salve, ointment or paste, must be made by one seeking to treat the malady on the particular animal. Therefore, the prior art compositions, and methods of use, suffer from the same disadvantage, i.e., the compositions are removed or worn off of the treated area when the animal is allowed to stand and/or walk around on the ground. To be effective, using prior art preparations, one must restrain or preclude the treated hoof from coming into contact with the ground.

It is therefore an object of this invention to provide a composition for treating the hooves of animals that exhibits the advantages of prior art compositions while avoiding the disadvantages of prior art compositions.

A second objective of this invention is to provide a method for the treatment of maladies found in the hooves of animals.

A further objective of this invention is to provide a method for the treatment of hoof maladies of animals without necessarily incapacitating the animal.

A still further objective of this invention is to provide a composition for the treatment of animal hooves that is suitable for direct and indirect application to the infected area that is economical and efficient.

Applicants know of no prior art compositions which totally meet the above-stated objectives.

THE INVENTION

Summary

In seeking to achieve the above-stated objectives, a novel composition and method for the treatment of animal hooves has been invented.

The composition is principally comprised of metallic sulfates in inert carriers suitable for application to animal hooves, and it may contain certain metallic oxides. It may be applied directly to the hoof of the animal, as prior art compounds, or preferably it may be indirectly applied to the animal hooves by broadcasting or seeding the ground with the material where hoof animals stand or walk.

When hoofed animals are alllowed to stand or walk on ground seeded with this invention, a noticable healing effect is achieved, bacteria are killed, and sole and frogs of the foot are hardened and thickened. Rain enhances the action of the composition when the ground has been seeded with the invention and the animal need not be confined to the area containing the preparation continously.

DETAILED DESCRIPTION

While there are numerous medicines and compounds employed in the treatment of animal hooves, none of these compounds are known to be suitable for indirect application to the hooves of animals as mentioned in the above-stated objectives of this invention.

A composition formed from readily available compounds, has been invented which achieves all of the above-stated objectives in a novel, useful and unobvious manner. This composition, containing the sulfates of copper, zinc and iron, an oxide of iron and an inert ingredient as a carrier, is preferably applied to the hooves of animals by "seeding" it on the ground, i.e, by "scattering or broadcasting" it in areas such as a corral.

The active ingredients may be seeded into the soil without a carrier. However, such a mixture would be very concentrated and care would have to be exercised to preclude it from causing the hooves to become too hard and too polished.

The active ingredients, of the mixture or composition, are gradually worked into the hooves of animals walking upon the "seeded" ground. The mixture starts to work, or become effective, in about one month. However, the animals can be in and out of the corral during this time, ie., they do not have to be confined within the corral at all times.

Rain actually enhances the effects of the composition, because sulfides come to the surface when the ground is wet or leached, ie., the sulfides float up. It is best to sprinkle water on the seeded soil once a week to promote this action.

Mixtures according to the invention may preferably be prepared by combining selected weight percentages of the following compounds:

TABLE I

| Item No. | Compound Name | Chemical Formula | Allowable Range, Wt. % |
|---|---|---|---|
| 1 | Copper Sulfate | $CuSO_4 \cdot 5H_2O$ | 0.04–55.00 |
| 2 | Zinc Sulfate | $ZnSO_4 \cdot H_2O$ | .15–5.06 |
| 3 | Iron Sulfate | $FeSO_4 \cdot 7H_2O$ | 2.00–25.00 |
| 4 | Manganese Sulfate | $MnSO_4 \cdot 4H_2O$ | .10–5.00 |

TABLE I-continued

| Item No. | Compound Name | Chemical Formula | Allowable Range, Wt. % |
|---|---|---|---|
| 5 | Inert Carrier | | .01–99.97 |

A preferred mixture comprises 0.94% $CuSO_4$, 0.24% $ZnSO_4$, 2.91% $FeSO_4$, 0.05% $MnSO_4$, and 95% inert carrier where the carrier is an inert NaCl salt having a moisture content of 3% or less. In another preferred mixture manganese sulfate might be eliminated.

Mixtures according to the invention may also be prepared by providing combinations of the following compounds in selected weight percentages:

TABLE II

| Item No. | Compound Name | Chemical Formula | Allowable Range, Wt. % |
|---|---|---|---|
| 1 | Copper Sulfate | $CuSO_4 \cdot 5H_2O$ | 0.04–50.00 |
| 2 | Zinc Sulfate | $ZnSO_4 \cdot H_2O$ | .15–5.06 |
| 3 | Iron Sulfate | $FeSO_4 \cdot 7H_2O$ | 2.00–20.00 |
| 4 | Iron Oxide | $Fe_2O_3$ | 6.50–10.00 |
| 5 | Manganese Sulfate | $MnSO_4 \cdot 4H_2O$ | .10–5.00 |
| 6 | Zinc Oxide (Red) | ZnO | .10–5.00 |
| 7 | Magnesium Oxide | MgO | .10–5.00 |
| 8 | Inert Carrier | | .01–99.97 |

A preferred mixture, using the compounds listed in Table II, comprises: 0.94% $CuSO_4$, 0.24% $ZnSO_4$, 2.91% $FeSO_4$, 1.69% $Fe_2O_3$, 0.05% $MnSO_4$, 0.06% ZnO, 0.02% MgO, and 94.09% inert carrier where the carrier is an inert NaCl salt having a moisture content of 3% or less.

Other inert carriers may be used such as sand, dirt, salves or ointments. Salves or ointments such as Lanolin, Bee's Wax, Silicone and Glycerin will function as excellent carriers. However, mixtures prepared with these carriers could not be broadcasted or seeded as those prepared with the salt, sand or dirt carriers.

Technical grade chemicals are suitable for the preparation of this invention. As such, trace amounts of other chemicals are present in the resulting formula or composition. For example; Iron Oxide obtained from McKesson Company and sold under the designation RED-NR-4284, contains only 82–86% $Fe_2O_3$. The balance is silica or one of the silicates. The preferred carrier, NaCl, obtained from the Western Salt Company of Los Angeles may contain; 0.047% acid insoluble matter, trace amounts of aluminum and Iron Oxides, 0.270% soldium carbonate, 0.730% sodium sulfate, 0.010% soldium borate and trace amounts of arsenic in addition to sodium chloride.

Each active ingredient is weighed into a blender and blended at 120° to 210° F. in a 30% or less moisture atmosphere from 10 minutes to 5 hours or until a homogenous mixture is obtained. After blending, the mixture is filtered through a sieve to achieve an even particle size distribution. If a dry inert carrier is employed, the carrier is also blended with the active ingredients in the same blender. Good blends are obtained via using ingredients whose mean particle diameters vary from dust or extra fines up to but not exceeding what is known as diamond crystals.

In the case of compositions designed to be applied directly to the animal hoof, a salve or ointment is mixed with the active ingredient blend in a blender. Wetting agents may or may not needed to achieve a homogenous active ingredient—inert carrier mixture depending upon the carrier selected. If Bee's Wax is used as a carrier, the mixture must be prepared at a temperature high enough to melt the wax.

A preferred method of using this invention is to spread (0.111 oz.), of the preferred composition, per square foot of ground where the hoofed animals stand or walk. The ground may be sprinkled lightly to enhance the initial absorption of the active ingredients. Later, sprinkling is employed to leach the active ingredients to the surface.

Within three months, it becomes necessary to re-seed the ground or soil to maintain the effect. Insomuch as this invention tends to harden and polish the hoof as well as exhibit curative properties when the hoof is infected, the maintenance of the effect is not harmful.

Having completely described our invention as well as how to make and use the invention, the scope of our claims may be understood as follows:

We claim:

1. A composition for the treatment of animal hooves, that is suitable for indirect application to said hooves by ground seeding techniques, comprised of a blend of an inert carrier selected from the group consisting of salt, sand and dirt, and a mixture of effective amounts of copper sulfate, zinc sulfate, and iron sulfate.

2. The composition of claim 1 wherein said carrier is NaCl.

3. A method of treating the hooves of numerous animals at one time comprised of: seeding a composition composed of a blend of an inert carrier and a mixture of effective amounts of copper sulfate, zinc sulfate, and iron sulfate onto the surface of an area where said animals will be allowed to walk, sprinkling said area with water, and causing said animals to walk or stand upon said surfaces at intermittent time intervals whereby the active ingredients of said mixture will contact said hooves.

4. The method of claim 3 wherein said inert carrier is selected from the group consisting of salt, sand and dirt.

5. The method according to claim 3 wherein said mixture includes an effective amount of manganese sulfate.

6. A composition for the treatment of animal hooves, that is suitable for indirect application to said hooves by ground seeding techniques, comprised of a blend of an inert carrier and a mixture of effective amounts of copper sulfate, zinc sulfate, iron sulfate, and magnesium sulfate.

7. The composition of claim 6 wherein said carrier is selected from the group consisting of salt, sand and dirt.

8. The composition of claim 7, wherein said carrier is NaCl.

9. The composition of claim 6, wherein said mixture further includes manganese sulfate.

10. A method of treating the hooves of numerous animals at one time comprised of: seeding a composition composed of a blend of an inert carrier and a mixture of effective amounts of copper sulfate, zinc sulfate, iron sulfate, and magnesium sulfate onto the surface of an area where said animals will be allowed to walk, sprinkling said area with water, and causing said animals to walk or stand upon said surfaces at intermittent time intervals whereby the active ingredients of said mixture will contact said hooves.

11. The method of claim 10, wherein said inert carrier is selected from the group consisting of salt, sand and dirt.

12. The method of claim 10, wherein said mixture further includes an effective amount of manganese sulfate.

* * * * *